United States Patent
Lee et al.

(10) Patent No.: US 10,591,415 B2
(45) Date of Patent: Mar. 17, 2020

(54) BIOCHIP INCLUDING SIDE EMITTING-TYPE LIGHT-EMITTING DEVICE AND FABRICATION METHOD THEREOF

(71) Applicant: OPTOLANE TECHNOLOGIES INC., Seongnam-si, Gyeonggi-do (KR)

(72) Inventors: Do Young Lee, Seongnam-si (KR); In Gyun Jeon, Seongnam-si (KR)

(73) Assignee: OPTOLANE TECHNOLOGIES INC., Seongnam-si, Gyeonggi-Do (KR)

( * ) Notice: Subject to any disclaimer, the term of this patent is extended or adjusted under 35 U.S.C. 154(b) by 0 days.

(21) Appl. No.: 16/001,056

(22) Filed: Jun. 6, 2018

(65) Prior Publication Data

US 2018/0284024 A1 Oct. 4, 2018

Related U.S. Application Data

(62) Division of application No. 14/824,764, filed on Aug. 12, 2015, now Pat. No. 10,018,562.

(30) Foreign Application Priority Data

Aug. 13, 2014 (KR) .................. 10-2014-0104908

(51) Int. Cl.
*G01N 21/64* (2006.01)
*H01L 31/12* (2006.01)
*H01L 31/18* (2006.01)

(52) U.S. Cl.
CPC ..... *G01N 21/6428* (2013.01); *G01N 21/6452* (2013.01); *G01N 21/6454* (2013.01); *G01N 21/6456* (2013.01); *H01L 31/125* (2013.01); *H01L 31/18* (2013.01); *G01N 2201/062* (2013.01)

(58) Field of Classification Search
None
See application file for complete search history.

(56) References Cited

U.S. PATENT DOCUMENTS

2012/0156100 A1* 6/2012 Tsai .................. G01N 21/6428
422/82.08

* cited by examiner

*Primary Examiner* — Jiong-Ping Lu
(74) *Attorney, Agent, or Firm* — Kile Park Reed & Houtteman PLLC

(57) ABSTRACT

The present disclosure a biochip including a side emitting-type light-emitting device, in which the bio-chip includes: a light-emitting device for emitting light from a fluorescent material; reflective layers provided over and under the light-emitting device so as to emit light from the sides of the light-emitting device; and reaction regions formed by etching of flanking regions of the light-emitting device. In the biochip, light emitted from the sides of the light-emitting device causes a biochemical reaction in the reaction regions. According to the present disclosure, light emitted from the light-emitting device moves only laterally without being transferred to the top or bottom of the bio-layer, and is transferred to the reaction regions formed by etching of flanking regions of the light-emitting device, so that a biochemical reaction in the reaction regions can be more efficiently performed.

7 Claims, 3 Drawing Sheets

BIOCHIP INCLUDING SIDE EMITTING-TYPE LIGHT-EMITTING DEVICE AND FABRICATION METHOD THEREOF

CROSS REFERENCE TO RELATED APPLICATIONS

This application is a divisional application of U.S. patent application Ser. No. 14/824,764, filed Aug. 12, 2015 (currently pending), the disclosure of which is herein incorporated by reference in its entirety. The U.S. patent application Ser. No. 14/824,764 claims priority to and the benefit of Korean Patent Application No. 10-2014-0104908 filed Aug. 13, 2014, which is hereby incorporated by reference for all purposes as if fully set forth herein.

BACKGROUND

1. Technical Field

The present disclosure relates to a biochip and a fabrication method thereof, and more particularly, to a biochip including a side emitting-type light-emitting device, in which light emitted from the sides of the light-emitting device included in a bio-layer can cause a biochemical reaction, and which can detect light emitted by the biochemical reaction to thereby provide biochemical information, and to a method for fabricating the biochip.

2. Related Art

In general, a biochip is formed by arraying reference samples including biological molecules such as DNA and proteins on a substrate made of a material such as glass, silicon, a metal such as gold, or nylon.

The biochip basically uses biochemical reactions between the reference sample fixed to the substrate and a target material. Representative examples of the biochemical reaction between the reference sample and the target sample include the complementary binding of DNA bases, and an antigen-antibody reaction.

Diagnoses using the biochip are generally performed by detecting the degree of a biochemical reaction between the reference sample and the target sample through an optical process. An optical process that is generally used is based on fluorescence or luminescence.

FIG. 1 shows a cross-sectional view of a conventional chip having an image sensor.

Referring to FIG. 1, a biochip 100 having an image sensor comprises a bio-layer 110, a filter layer 120 and an image sensor layer 130.

The bio-layer 110 is a layer in which a biochemical reaction between a reference sample and a target sample takes place. In addition, as a result of the biochemical reaction, a luminescent or fluorescent material remains in the bio-layer 110.

In the case in which a luminescent material remains in the bio-layer 110, it is required to block external light, because the luminescent material itself emits light. However, in the case in which a fluorescent material remains in the bio-layer 110, separate external light is required to emit light from the fluorescent material. Thus, in this case, a filter layer is required to block the external light from being incident to the image sensor layer.

The filter layer 120 is formed under the bio-layer 110. The filter layer functions to block the external light from being incident to the image sensor layer disposed under the filter layer, when a fluorescent material remains as a result of the biochemical reaction.

In other words, the external light acts as noise in a process of measuring the fluorescence of the fluorescent material by the image sensor layer. Thus, the filter layer functions to remove the external light that is noise.

The image sensor layer 130 is formed under the filter layer 120, and comprises a plurality of photodetectors 131. The plurality of photodetectors 131 functions to detect the light filtered by the filter layer and to convert the detected light into an electrical signal.

However, the conventional biochip 100 as described above has shortcomings in that the difference between the wavelength ($\lambda_f$) of the external light and the wavelength ($\lambda_E$) of light emitted from the luminescent or fluorescent material is very small and in that it is required to design a precise filter layer 120 capable of filtering out light corresponding to this small difference.

SUMMARY

Various embodiments are directed to a biochip including a side emitting-type light-emitting device, in which the bio-chip includes: a light-emitting device comprising a light-emitting region for emitting light from a fluorescent material, and reflective layers provided over and under the light-emitting region so as to emit light from the sides of the light-emitting device; and reaction regions formed by etching of flanking regions of the light-emitting device so that light emitted from the sides of the light-emitting device will cause a biochemical reaction in the reaction regions.

Also, various embodiments are directed to a method for fabricating a biochip including a side emitting-type light-emitting device, which is configured such that light emitted from the sides of the light-emitting device causes a biochemical reaction in reaction regions.

In an embodiment, a biochip including a side emitting-type light-emitting device includes: a bio-layer having formed therein a plurality of reaction regions in which a biochemical reaction between a reference sample and a target sample occurs; and an image sensor layer formed under the bio-layer and having formed therein a plurality of photodetectors, wherein the side emitting-type light-emitting device is disposed in the bio-layer, and light emitted from the sides of the side emitting-type light-emitting device is incident to the plurality of reaction regions.

In another embodiment, a method for fabricating a biochip including a side emitting-type light-emitting device includes the steps of: (S100) forming an image sensor layer; (S200) forming a bio-layer; and (S300) depositing a bio-layer, wherein step (S200) of forming the bio-layer includes the steps of: (S210) forming a light-emitting device layer; and (S220) forming reaction regions.

DETAILED DESCRIPTION

Hereinafter, exemplary embodiments of the present disclosure will be described in detail with reference to the accompanying drawings.

Figure 1:
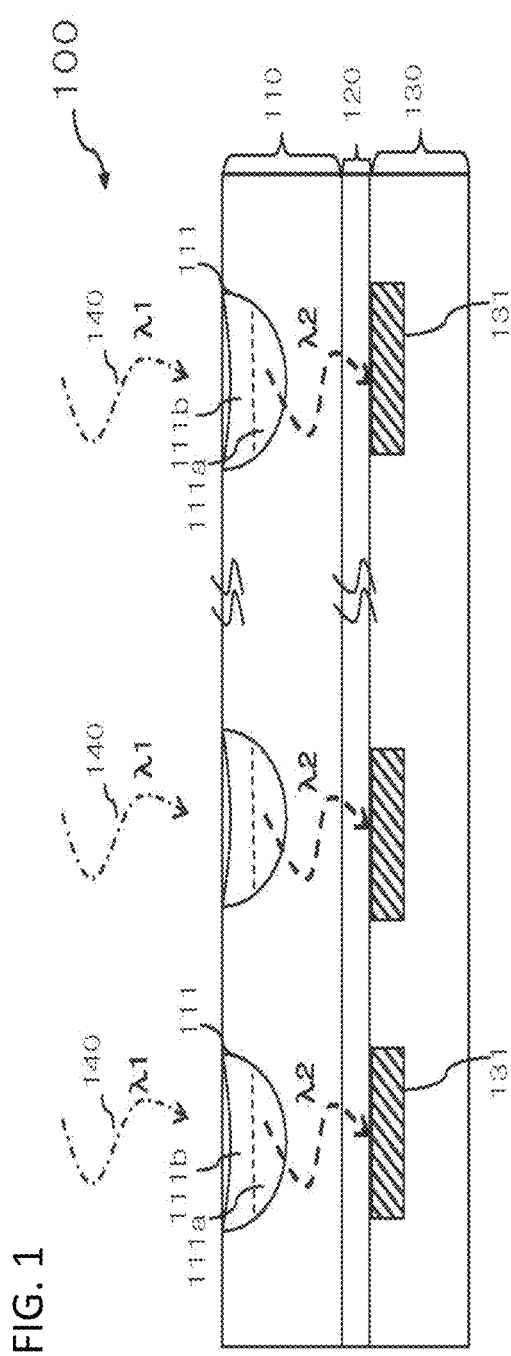
FIG. 1 shows a cross-sectional view of a conventional biochip having an image sensor.
Figure 2:
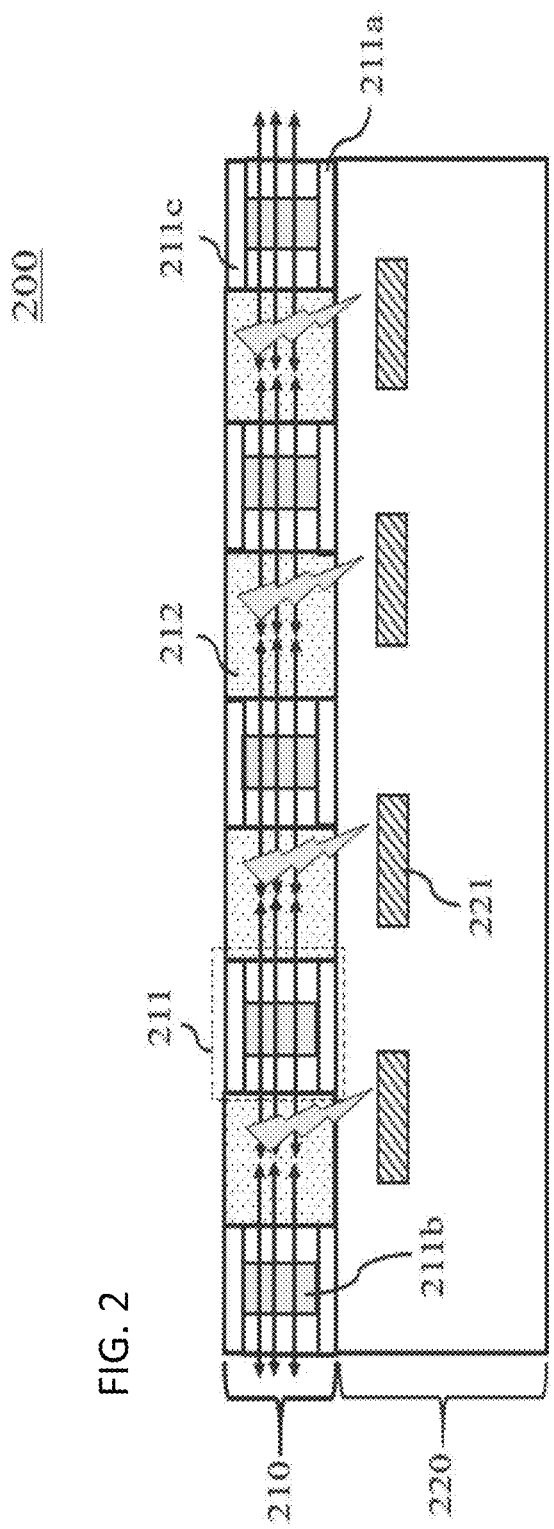
FIG. 2 shows a cross-sectional view of a biochip including a side emitting-type light-emitting device according to the present disclosure.

FIG. 2 shows a cross-sectional view of a biochip including a side emitting-type light-emitting device according to the present disclosure.

Referring to FIG. 2, a biochip 200 including a side emitting-type light-emitting device according to the present disclosure comprises a bio-layer 210 and an image sensor layer 220.

The bio-layer 210 comprises a plurality of light-emitting devices 211 and a plurality of reaction regions 212.

Each of the light-emitting devices 211 comprises a first reflective layer 211a, a light-emitting region 211b and a second reflective layer 211c.

The plurality of reaction regions 212 is formed by etching regions excluding regions in which the light-emitting devices 211 are formed in the bio-layer 210, and is a place in which a biochemical reaction between a reference sample and a target sample occurs. The biochemical reaction occurs when the target sample is added to the reaction regions 212 containing the reference sample.

The reference sample is selected from various types of samples that are able to biochemically react with the target sample. The type of reference sample varies depending on the type of biochemical reaction intended in the biochip. For example, if the biochemical reaction is an antigen-antibody reaction, the reference sample may be an antigen.

The type of target sample is determined according to the type of reference sample. For example, if the reference sample is an antigen, the target ample may be blood or the like.

The light-emitting device 211 is connected with a peripheral circuit that can emit light at a certain wavelength and that can control on-off switching or the like. The light-emitting device 211 is preferably a light-emitting diode (LED) that emits light upon application of current and that has excellent light emission efficiency.

Herein, the first reflective layer 211a is positioned under the light-emitting region 211b, and the second reflective layer 211c is positioned over the light-emitting region 211b. The first reflective layer 211a and the second reflective layer 211c functions as a blocking layer that allows light emitted from the light-emitting region 211b to be directed to the side without being directed upward and downward.

Due to these reflective layers, light emitted from the light-emitting device 211 is not incident to the top and bottom of the bio-layer 210. In other words, the emitted light is not incident to the image sensor layer 220, but is directed only to the plurality of reaction regions 212 formed at the sides of the light-emitting devices 211.

Meanwhile, no reflective layer is formed over the light-emitting device, if required, so that light emitted from the light-emitting device can be incident to the top of the bio-layer 210.

Although not shown in the figures, a filter layer for blocking light emitted from the light-emitting device 211 may further be formed between the bio-layer 210 and the image sensor layer 220. The filter layer together with the first reflective layer 211a functions to block light emitted from the light-emitting region 211b from being incident to the image sensor layer 220 and to allow only fluorescent light, generated by a biochemical reaction in the reaction region 212, to be incident to the image sensor layer. The image sensor layer 220 is formed under the bio-layer 210 and comprises a plurality of photodetectors 221.

The plurality of photodetectors 221 is formed on the surface of the image sensor layer 220 and functions to detect light and to produce a charge corresponding to the detected light. To each of the plurality of photodetectors 221, a peripheral circuit for producing an electrical signal based on the produced charge is connected. Typical examples of the plurality of photodetectors 221 include charge-coupled device (CCD) type image sensors and complementary MOS (CMOS) type image sensors.

The plurality of reaction regions 212 is formed by an etching process on bio-layer regions in which the light-emitting devices 211 are not formed. The etching process may be performed using various methods such as wet etching or dry etching.

Meanwhile, the reaction regions that are formed by etching may have various shapes. Specifically, the reaction regions may be formed using a conventional method such as slope etching so as to have a slanted shape, or may be formed by a multi-step etching process so as to have a stepped portion.

Figure 3:
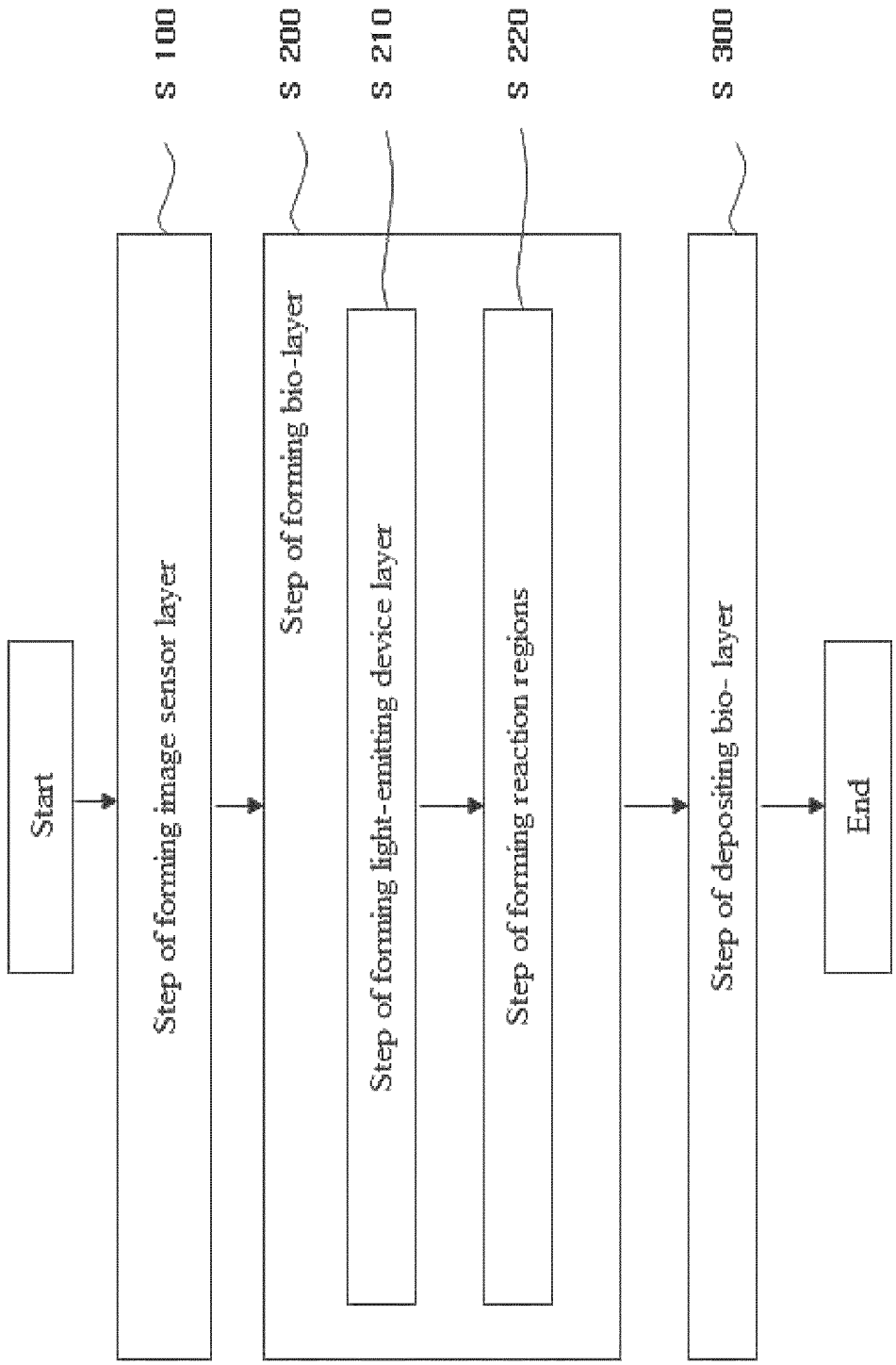
FIG. 3 is a process flowchart showing a method for fabricating a side emitting-type light-emitting device according to the present disclosure.

FIG. 3 is a process flow chart showing a method for fabricating a biochip including a side emitting-type light-emitting device according to the present disclosure.

Referring to FIG. 3, a method for fabricating a biochip including a side emitting-type light-emitting device according to the present disclosure comprises the steps of: (S100) forming an image sensor layer; (S200) forming a bio-layer; and (S300) depositing the bio-layer.

In step (S100) of forming an image sensor layer, an image sensor layer comprising a plurality of photodetectors is formed on a semiconductor substrate, and in step (S200) of forming a bio-layer, a bio-layer, comprising side emitting-type light-emitting devices and a plurality of reaction regions, is formed on a substrate.

Step (S200) of forming the bio-layer comprises the steps of: (S210) forming a light-emitting device layer; and (S220) forming reaction regions.

In step (S210) of forming the light-emitting device layer, a light-emitting device layer having formed therein a plurality of light-emitting devices, each comprising a reflective layer formed over and under a light-emitting region, is formed.

Specifically, a first reflective layer, a light-emitting region and a second reflective layer are sequentially formed on the substrate, thereby forming a light-emitting device layer.

The first reflective layer and the second reflective layer may be made of any material that prevents light emitted from the light-emitting device from being incident to the top or bottom of the bio-layer.

In step (S220) of forming reaction regions, a plurality of reaction regions is formed by dry- or wet-etching of flanking regions of the light-emitting device layer portions in which the light-emitting regions were formed.

Specifically, a plurality of reaction regions can be formed by etching the light-emitting device layer portions in which the light-emitting devices were not formed, in such a manner that the reaction regions pass through the second reflective layer and the first reflective layer.

Meanwhile, step (S220) of forming the reaction regions can be performed by dry or wet etching. In addition, step (S220) of forming the reaction regions can be performed by a multi-step etching process such that the reaction region has a plurality of stepped portions. Alternatively, step (S220) of forming the reaction regions can be performed by slope etching such that the reaction region has a slanted shape.

Next, step (S300) of depositing the bio-layer is performed. In step (S300), the bio-layer is deposited on the image sensor layer, thereby fabricating the biochip including the side emitting-type light-emitting device according to the present disclosure.

After the step of forming the reaction regions, but before the step of depositing the bio-layer on the image sensor layer, the substrate may be removed from the bio-layer so that a biochemical reaction occurring in the reaction regions can be more accurately detected by the image sensor layer.

Meanwhile, the method of the present disclosure may further comprise a step of forming a filter layer, which functions to block light emitted from the light-emitting device, between the bio-layer 210 and the image sensor layer 220.

Herein, the filter layer may be formed on the image sensor layer in the step of forming the image sensor layer. Alternatively, the filter layer may be formed on the substrate in the step of forming the bio-layer before the step of forming the light-emitting device layer.

Specifically, the filter layer may be formed on the image sensor layer, and then the bio-layer may be deposited thereon. Alternatively, the filter layer may be formed on the bottom surface, and then deposited on the image sensor layer.

In the biochip including the side emitting-type light-emitting device according to the present disclosure, the reaction regions are not formed on the top surface of the bio-layer, but are formed so as to extend from the top to the bottom of the bio-layer, unlike the prior art. Thus, light emitted from the sides of the light-emitting devices will be incident to the plurality of reaction regions, and a biochemical reaction between a reference sample and a target sample will occur in the plurality of reaction regions.

Meanwhile, in the process of forming the plurality of reaction regions by etching, the reaction regions can be formed to have various shapes. Specifically, the reaction regions can be formed using a conventional method such as slope etching so as to have a slanted shape, or can be formed by a multi-step etching process so as to have stepped portions.

As described above, the biochip according to the present disclosure includes the side emitting-type light-emitting devices provided in the bio-layer, and comprises the reaction regions formed to extend to the bottom of the bio-layer. Thus, light emitted from the side emitting-type light-emitting devices is incident to the reaction regions to cause a biochemical reaction.

Light emitted from the side emitting-type light-emitting devices according to the present disclosure is completely incident to the reaction regions formed at the sides of the light-emitting devices without being incident to the top of the bio-layer or the image sensor layer, so that a biochemical reaction between a reference sample and a target sample in the region regions can more actively occur.

In other words, in the biochip including the side emitting-type light-emitting device according to the present disclosure, light emitted from the light-emitting device moves only laterally without being transferred to the top or bottom of the bio-layer, and is transferred to the reaction regions formed by etching of flanking regions of the light-emitting device, so that a biochemical reaction in the reaction regions can be more efficiently performed.

While various embodiments have been described above, it will be understood to those skilled in the art that the embodiments described are by way of example only. Accordingly, the disclosure described herein should not be limited based on the described embodiments.

What is claimed is:

1. A method for fabricating a biochip including a side emitting light-emitting device, the method comprising the steps of:
    forming on a semiconductor substrate an image sensor layer having a plurality of photodetectors;
    forming a bio-layer having a light-emitting device and a plurality of reaction regions; and
    depositing the bio-layer over the image sensor layer,
    wherein the step of forming the bio-layer comprises the steps of:
        forming a light-emitting device layer having formed therein a plurality of the light-emitting devices, each having reflective layers over and under a light-emitting region; and
        forming the plurality of reaction regions by etching light-emitting device layer portions in which the light-emitting devices were not formed,
    wherein the step of forming the light-emitting device layer comprises the steps of:
        forming a first reflective layer on a substrate;
        forming on portions of the first reflective layer a light-emitting layer having the light-emitting regions; and
        forming a second reflective layer on the light-emitting layer,
    wherein the step of forming the reaction regions is a step of forming the reaction regions passing through the second reflective layer, the light-emitting device layer and the first reflective layer by dry- or wet-etching of the light-emitting device layer portions in which the light-emitting device was not formed.

2. The method of claim 1, wherein the step of forming the reaction regions is a step of forming the reaction regions by a multi-step etching process so as to have a stepped portion.

3. The method of claim 1, wherein the step of forming the reaction regions is a step of forming the reaction regions by slope etching so as to have a slanted shape.

4. The method of claim 1, further comprising, after the step of forming the reaction regions, but before the step of depositing the bio-layer on the image sensor layer, a step of removing the substrate from the bio-layer.

5. The method of claim 1, wherein the step of forming the image sensor layer further comprises a step of forming a filter layer on the image sensor layer.

6. The method of claim 1, wherein the step of forming the bio-layer further comprises, before the step of forming the light-emitting device layer, a step of forming a filter layer on the substrate.

7. The method of claim 6, wherein the step of depositing the bio-layer is a step of depositing the bio-layer in such a manner that the filter layer formed under the bio-layer is placed on the image sensor layer.

* * * * *